United States Patent [19]

Blumenfeld

[11] B 4,000,052

[45] Dec. 28, 1976

[54] METHOD OF PREPARING METHYLCHLOROMETHYLTETRA- CHLOROBENZENES AND DI-(CHLOROMETHYL)-TETRACHLORO- BENZENES

[75] Inventor: Georg Blumenfeld, St. Augustin, Germany

[73] Assignee: Dynamit Nobel Aktiengesellschaft, Troisdorf, Germany

[22] Filed: Nov. 22, 1974

[21] Appl. No.: 526,447

[44] Published under the second Trial Voluntary Protest Program on February 24, 1976 as document No. B 526,447.

[30] Foreign Application Priority Data

Nov. 27, 1973 Germany ............................ 2358949

[52] U.S. Cl. ............................................ 204/163 R
[51] Int. Cl.$^2$ ............................................ B01J 1/10
[58] Field of Search ................................ 204/163 R

[56] References Cited

FOREIGN PATENTS OR APPLICATIONS 1,568,607   3/1970   Germany ............................ 204/163

Primary Examiner—Howard S. Williams
Attorney, Agent, or Firm—Burgess, Dinklage & Sprung

[57] ABSTRACT

A process for preparing a chloromethyl-tetrachloro-benzene which comprises the steps of:

A. Contacting a xylene in a chlorine resistant solvent with 0.5 to 2, preferably 1 to 2 weight percent of FeCl$_3$, based upon the weight of said xylene, at a temperature of 20 to 70° C in the absence of light in a vessel having a vapor space over the level of the xylene solution.

B. Introducing into said vapor space chlorine and passing the same over said solution while strongly agitating the solution, said chlorine being introduced such that an excess pressure of 0.01 to 1 atmosphere exists over said solution;

C. Maintaining said solution at said temperature of 20 to 70° C for a period of time at least 0.5 hours, preferably between 3 and 6 hours;

D. Thereafter directing energy-rich light at said vapor space while adding chlorine into said vapor space and maintaining the excess pressure over said solution at 0.01 to 1 atmosphere while maintaining the solution at a temperature of 50° to 80° C for a period of time of at least 0.5 hours, preferably between 4 and 7 hours and while continuing said agitation; and E. Separating and recovering a chloromethyltetra-chlorobenzene.

10 Claims, No Drawings

METHOD OF PREPARING METHYLCHLOROMETHYLTETRACHLOROBENZENES AND DI-(CHLOROMETHYL)-TETRACHLOROBENZENES

BACKGROUND OF THE INVENTION

1. Field of the Invention

This invention relates to a process for the preparation of chloromethyltetrachlorobenzenes and particularly to the preparation of methylchloromethyltetrachlorobenzenes and/or di-(chloromethyl)-tetrachlorobenzenes by the chlorination of xylenes. This invention is particularly directed to a highly selective process for the preparation of said chloromethyltetrachlorobenzenes whereby photochlorination is effected by directing the chlorine gas into a vapor space above a xylene solution and agitating the solution while directing a source of high energy light at such vapor space. This invention is also directed to such a process whereby high yields of the chloromethyltetrachlorobenzenes are recovered at high purities.

2. Discussion of the Prior Art

According to the U.S. Pat. No. 2,412,389, it is known to chlorinate p-xylene in the presence of $FeCl_3$ in $CCl_4$ to prepare 1,4-dimethyl-2,3,5,6-tetrachlorobenzene, and after the removal of the $FeCl_3$, to chlorinate the latter with irradiation and refluxing in $CCl_4$ to form 1,4-di-(chloromethyl)-2,3,5,6-tetrachlorobenzene. According to Belgian Pat. No. 631,170, it is likewise known first to prepare 1,3-dimethyl-2,4,5,6-tetrachlorobenzene from m-xylene, and 1,2-dimethyl-3,4,5,6-tetrachlorobenzene from o-xylene, and to prepare from these, by photochlorination, 1,3-di-(chloromethyl)-2,4,5,6-tetrachlorobenzene and 1,2-di-(chloromethyl)-3,4,5,6-tetrachlorobenzene, respectively.

German Pat. No. 1,568,607 describes a method of chlorinating xylenes in the presence of $FeCl_3$ to form tetrachloroxylenes, and then, in a second reaction, without removal of the $FeCl_3$, performing further chlorination with irradiation with high-energy light to form di-(chloromethyl)-tetrachlorobenzenes.

In comparison with the process of U.S. Pat. No. 2,412,389 and Belgian Pat. No. 631,170, in which the xylene chlorinated in the nucleus is isolated, refined, and then photochlorinated to di-(chloromethyl)-tetrachlorobenzenes, the process of German Pat. No. 1,568,607 appears to represent an advance in that the xylene chlorinated in the nucleus is not isolated, but is photochlorinated in the form of a suspension in $CCl_4$ containing ferric chloride to produce di-(chloromethyl)-tetrachlorobenzene. The photochlorination requires that the ferric chloride concentration be as low as possible. The German Pat. No. 1,568,607 recommends 0.05 to 1.0 weight percent $FeCl_3$ with respect to xylene, in order to minimize the absorption of the light required for the activation of chlorine.

However, due to the fact that the side-chain chlorination must take place in the presence of low amounts of ferric chloride the reaction requires operations with a high chlorine input rate (0.4 to 1.6 parts by weight per weight-part of xylene per hour). This high chlorine input makes up for the decrease in the output of catalyst. In an example given for purposes of comparison in German Pat. No. 1,568,607 it is shown what a disadvantageous effect a slower introduction of chlorine has on the yield of dimethyltetrachlorobenzene under otherwise the same conditions. On the other hand, it is generally known that the slower the introduction of chlorine is under otherwise the same conditions, the more fully it is utilized.

The chlorine utilization in the nuclear chlorination of xylene pursuant to German Pat. No. 1,568,607 is accordingly poor. 140% of the stoichiometric amount of chlorine is required.

In the side-chain photochlorination to di-(chloromethyl)-tetrachlorobenzene of German Pat. No. 1,568,607, chlorine is introduced (evidently for better chlorine utilization) at a rate that is one-third to two-thirds lower than the rate required for the chlorination in the nucleus, with heating and irradiation from a submerged ultraviolet lamp of 80 W.

According to German Pat. No. 1,568,607, this procedure is said to produce 1,4-di-(chloromethyl)-tetrachlorobenzene in a 98.5% yield, but efforts to confirm this have proven unsuccessful. Although the conditions specified for the chlorination in the nucleus were accurately created as specified in the patent, and the side-chain chlorination was performed at half of the chlorine introduction rate, even using 200% of the calculated stoichiometric amount of chlorine (German Pat. No. 1,568,607 recommends one-third to two-thirds of the nuclear chlorination rate for the side-chain chlorination, which in Example 2, at 5 hours of chlorine feeding, amounts to 133 to 266% of the calculated amounted of chlorine), only 10.6% 1,4-dimethyltetrachlorobenzene, 74.4% 1-methyl-4-chloromethyltetrachlorobenzene, and 13.7% 1,4-di-(chloromethyl)-tetrachlorobenzene were obtained.

Apparently, if the teaching of German Pat. No. 1,568,607 is followed, the transformation and the reaction rate of the side-chain photochlorination are low on account of the absorption of the high-energy light by the ferric chloride present in the solution during the photochlorination.

It has therefore become desirable to provide a process for the preparation of chloromethyltetrachlorobenzenes whereby the intermediate product obtained from the nuclear chlorination need not be recovered and refined prior to photochlorination of the side-chain. It has become desirable, however, to provide a process which can be conducted in a sequential manner whereby the amount of chlorine employed is minimized. It has also become desirable to provide a process which is selective in respect of the desired chloromethyltetrachlorobenzene. It has become particularly desirable to provide a process in which the amount of chlorine employed will not exceed about 130% of the stoichiometric amount and yet provide yields of the desired chloromethyltetrachlorobenzene in excess of 60%.

SUMMARY OF THE INVENTION

The objects of the invention are provided by a process for the preparation of chloromethyltetrachlorobenzenes which comprises the steps of:

A. Contacting a xylene in a chlorine resistant solvent with 0.5 to 2, preferably 1 to 2 weight percent of $FeCl_3$, based upon the weight of said xylene, at a temperature of 20° to 70°C in the absence of energy-rich light in a vessel having a vapor space over the level of the xylene solution;

B. Introducing into said vapor space chlorine gas and maintaining the same over said solution while strongly agitating the solution, said chlorine being introduced such that an excess pressure of 0.01 to 1 atmospheres exists over said solution;

C. Maintaining said solution at said temperature of 20° to 70°C for a period of time of at least 0.5 hours between 3 and 6 hours;

D. Thereafter directing energy-rich light at said vapor space while adding chlorine into said vapor space and maintaining the excess pressure over said solution at 0.01 to 1 atmospheres while maintaining the solution at a temperature of 50° to 80°C for a period of time of at least 0.5 hours, preferably of 4 to 7 hours and while continuing said agitation; and E. Separating and recovering a chloromethyltetrachlorobenzene.

The process of the present invention proceeds in marked contrast to the procedures recommended by German Pat. No. 1,568,607. Whereas that patent disclosed introducing the chlorine into the liquid phase containing the ferric chloride and irradiating the liquid phase employing a submerged lamp, the present invention obtains high yields of the desired chloromethyltetrachlorobenzene by introducing the chlorine into the vapor space above the xylene solution rather than by introducing the same into the xylene solution. The solution is agitated rapidly as by stirring and a chlorine pressure is maintained over the solution such that the excess pressure, i.e., pressure above the normal atmosphere pressure, amounts to 0.01 to 1 atmospheres.

The process is generally a sequential process in which in a first phase the nuclear chlorination takes place. Nuclear chlorination takes place in accordance with the invention using a generally larger quantity of ferric chloride catalyst, say, an amount of 1 to 2 weight percent based upon the weight of the xylene. During this nuclear chlorination no light is directed against either the vapor space above the xylene solution or the xylene solution itself. After the nuclear chlorination is complete, which generally takes between about 3 and 6 hours, the photochlorination step is commenced.

Photochlorination is conducted by directing additional chlorine gas to the vapor space above the xylene solution. Agitation is continued so as to facilitate a transfer of the chlorine and any HCl into the xylene solution. In contrast to irradiating the solution where it is theorized that the reaction takes place, the vapor phase above the solution is irradiated. By performing such a process the desired chloromethyltetrachlorobenzenes are prepared in exceptionally high yields at exceptionally high purities.

For instance, the present invention can be conducted employing large amounts of ferric chloride catalysts relative to the xylene. As revealed in the examples below by contacting a xylene such as paraxylene with 2 weight percent ferric chloride and by conducting the sequential reaction steps as disclosed herein a yield of p-di-(chloromethyl)-tetrachlorobenzene of 84% can be realized and the same can be realized in a purity of 99.45%. This is in sharp contrast to the unselective process of German Pat. No. 1,568,607 which provides yields of p-di-(chloromethyl)-tetrachlorobenzene of only 13.7%.

The process is conducted employing either o-xylene, m-xylene or p-xylene and the manipulative steps do not vary from one isomer to another. The nuclear chlorination is conducted by forming a xylene solution in a chlorine resistant solvent, typically carbon tetrachloride. Into the resultant solution is charged between 1 and 2 weight percent of ferric chloride catalyst. The solution is maintained in a vessel which provides a vapor space thereabove, i.e., a vessel which is not filled to the brim with solution and ferric chloride. Chlorine gas is directed into the vapor space in the region above the solution. The solution is agitated. The agitation is suitably performed by a stirring operation and the agitation should be strong. It is desired that the agitation be such as to provide a maximum of intensity without substantial liquid splashing into the vapor phase. This degree of agitation insures the desired contact between the chlorine gas and the components in solution.

The solution is heated at a temperature between 20° and 70°C for at least 0.5 hours, preferably between about 3 and 6 hours, with the exclusion of light, particularly with the exclusion of light having high forms of energy.

After the xylene has become fully ring chlorinated, i.e., after the same has been converted into a di-methyltetrachlorobenzene a source of high energy light is directed at the vapor space above the solution. Additional chlorine is admitted into this space or zone for the purpose of effecting the photochlorination of the side chain. The photochlorination is carried out for a period of time of at least 0.5 hours between 4 and 7 hours. The rate of chlorine addition into the space is such that the pressure above atmospheric pressure, i.e., the excess pressure (also known as the gauge pressure) is between 0.01 and 1 atmospheres. This pressure paramater applies both to the ring chlorination and to the side chain chlorination. The reaction temperatures are adjusted, during the photochlorination, to a temperature in the liquid phase of 50° to 80°C, preferably between 50° and 70°C.

At the heart of the present invention there is the surprising finding that sufficient chlorine atoms enter the liquid phase in addition to diatomic chlorine molecules to commence the photochlorination and to maintain the same in progress. The transformation and the reaction rate of the photochlorination are independent of the ferric chloride concentration in the liquid phase and are independent of other light absorbing substances. It is particularly advantageous that the chlorination of the nucleus, which precedes the photochlorination, can be performed employing quantities of ferric chloride which provide optimum utilization of the chlorine admitted to the reaction system during that ring chlorination. Thus, in the process of the invention, yields of more than 80% of di-(chloromethyl)-tetrachlorobenzene can be obtained using a stoichiometric amount of chlorine of not more than 130%. Additionally, this process offers the additional advantage over known methods of preparing chloromethyl tetrachlorobenzenes that the line through which the chlorine gas passes becomes free of solid chlorination products which tends to form in the line. It has been experienced that where a chlorine line passes directly into the liquid phase containing the xylene that solid chlorination products can accumulate at the mouth of the chlorine lines whereby to clog the same and to create an uneven flow of chlorine and back pressure within the chlorine, thus further complicating the process.

DESCRIPTION OF PREFERRED EMBODIMENTS

The process is conducted initially by forming a solution of a xylene in a chlorine-resistant organic solvent. By the term "chlorine-resistant organic solvent" there is meant a substance which does not react with the chlorine introduced into the vapor space above the solutions under the conditions of the process and thus does not either absorb the chlorine or form a substitution product which can interfere with the reaction. Typically, a perchlorinated organic solvent can be used as typified by carbon tetrachloride. Additional solvents include perchlorobutadiene, trichloromethane (chloroform), O-dichlorobenzene and asymmetrical trichlorobenzene.

In the second phase of the process high energy light is directed against the vapors in the vapor space above the xylene solution. It is important that the light give off light rays having a wavelength of between 180 and 3,900 angstroms. Such high energy light can be derived from a 250-watt mercury vapor lamp (HR LS-Lampe made by Radium). Such a mercury vapor lamp can be mounted at a distance of approximately 10 cm. from the reaction vessel. Generally speaking, the light source will be mounted between 5 and 20 cm. from the reaction vessel depending upon the wavelength of the light given off by the light source. To prevent radiation losses, the lamp and reaction vessels can be enveloped in a protective foil such as a protective aluminum foil. High energy light can also be produced from light sources of other wattage made by other manufacturers, it being important to produce radiation of short wavelength typically ultraviolet radiation. Generally speaking, ultraviolet light has wavelengths between 180 and 3,900 angstroms.

While the process has been described above as utilizing elevated pressures of between 0.01 and 1 atmosphere and temperatures of 20–70°C in the nuclear chlorination step and 50°–80°C in the side chain photochlorination step, higher temperatures and pressures can also be employed. The temperatures and pressures are somewhat interrelated with one another and also depend to some extent on the particular xylene and inert solvent employed.

It has been found advantageous to perform the nuclear chlorination initially at 20°C, and to increase the temperature to 40°C in the second half of the reaction, for the avoidance of secondary reactions. The chlorination rate amounts to 0.5 to 1 weight part of chlorine per weight part of xylene per hour, depending on how the agitation is performed. The hydrogen chloride that escapes contains lesser amounts of chlorine than in the process of German Pat. No. 1,568,607. After 100% of the amount of chlorine necessary for the chlorination of xylene in the nucleus has been introduced, chlorine is introduced while the temperature of the liquid phase is 40° to 80°C, preferably 50° to 70°C, while the gas phase is irradiated with energy-rich light.

A special advantage of the process of the invention consists in the fact that the chlorination does not go beyond the chlorination of the di-(chloromethyl)-tetrachlorobenzene.

The methylchloromethyltetrachlorobenzenes and di-(chloromethyl)-tetrachlorobenzenes prepeared in accordance with the invention are valuable intermediates for the preparation of compounds of high molecular weight and of flameproofing agents.

In order to more fully illustrate the nature of the invention and the manner of practicing the same the following examples are presented. In the ensuing examples unless otherwise specified where reference is made to amounts in terms of percentage compositions, these are amounts referring to the various substances in mole percent. The yields which are stated refer to the theoretical values to be expected in the reaction with xylene.

EXAMPLE 1

1,4-di-(chloromethyl)-2,3,5,6-tetrachlorobenzene 212 g of p-xylene in 2000 ml of $CCl_4$ was chlorinated in the nucleus in the presence of 4 g of $FeCl_3$ by passing chlorine over the reaction solution, while stirring the latter, at a pressure of 0.06 atmospheres excess pressure with the exclusion of light. The first half of the amount of chlorine calculated for dimethyltetrachlorobenzene was introduced into the gas chamber of the reaction vessel when the temperature of the liquid phase was 20°C, and the rest when it was 40°C. The reaction time was approximately 3 hours. Then, while the gas chamber in the reaction vessel was exposed to the light from a 250-watt mercury vapor lamp, the side-chain chlorination was performed with the liquid phase temperature at 70°C, and required 7 hours to complete. Total chlorine consumption: 130% of the calculated amount, with respect to xylene. After cooling the reaction solution, the precipitated p-di-(chloromethyl)-tetrachlorobenzene was suction filtered, washed free of $FeCl_3$ with water, and dried. In this manner, 528 g of p-di-(chloromethyl)-tetrachlorobenzene was obtained in a purity of 99.45% (yield 84.2%).

EXAMPLE 2

1,2-di-(chloromethyl)-3,4,5,6-tetrachlorobenzene 212 g of o-xylene in 2,000 ml of $CCl_4$ was chlorinated in the nucleus in the presence of 4 g of $FeCl_3$ by passing chlorine over the reaction solution, with stirring, at a pressure of 0.06 atmospheres excess pressure with the exclusion of light. The first half of the amount of chlorine calculated for dimethyltetrachlorobenzene was introduced into the gas chamber of the reaction vessel at a liquid phase temperature of 20°C, and the remainder at 40°C. The reaction time was 3 hours. Then, while the gas chamber within the reaction vessel was irradiated from a 250-watt mercury vapor lamp, the side-chain chlorination was performed at a liquid phase temperature of 70°C. This operation was completed in about 7 hours. Total chlorine consumption: 130% of the calculated amount, with respect to xylene.

After the reaction solution had cooled, the precipitated o-di-(chloromethyl)-tetrachlorobenzene was suction filtered, washed free of $FeCl_3$ with water, and dried. 400 g of crude o-di-(chloromethyl)-tetrachlorobenzene was obtained in a purity of 80.6%.

Distillation of the filtrate produced an additional 200 g of o-di-(chloromethyl)-tetrachlorobenzene in a purity of 88%. The product, after recrystallization from acetone, melted at 83°–84°C. The total yield was 80%.

EXAMPLE 3

1,3-di-(chloromethyl)-2,4,5,6-tetrachlorobenzene 212 g of m-xylene in 2,000 ml of $CCl_4$ was chlorinated in the nucleus in the presence of 4 g of $FeCl_3$ by passing chlorine over the reaction solution, while the latter was being stirred, at a pressure of 0.06 atmospheres excess pressure, with the exclusion of light. The first half of the amount of chlorine calculated for dimethyltetrachlorobenzene was introduced into the gas chamber of the reaction vessel at a temperature in the liquid phase of 20°C, the remainder at 40°C. Then the side-chain chlorination was performed while irradiating the gas chamber in the reaction vessel with a 250-watt mercury vapor lamp, at a liquid phase temperature of 70°C and 0.06 atmospheres excess pressure. This side-chain chlorination was completed in 7 hours. Total chlorine consumption: 130% of the calculated amount, with respect to xylene. After the reaction solution had cooled, the precipitated m-di-(chloromethyl)-tetrachlorobenzene was suction filtered, washed free of $FeCl_3$ with water, and dried. 280 g of m-di-(chloromethyl)-tetrachlorobenzene was obtained in a purity of 89.5%, the yield being 40%. 310 additional grams of m-di-(chloromethyl)-tetrachlorobenzene were isolated from the filtrate by distillation, corresponding to an additional yield of 23%. 1-methyl-3-chloromethyl-2,4,5,6-tetrachlorobenzene, pentachlorotoluene, and pentachlorobenzylchloride also formed as additional products of the reaction.

EXAMPLE 4

1-methyl-3-chloromethyl-2,4,5,6-tetrachlorobenzene 530 g of m-xylene in 5 liters of $CCl_4$ was chlorinated in the nucleus in the presence of 10 g of $FeCl_3$ by passing chlorine over the reaction solution while stirring the latter, at a pressure of 0.06 atmospheres excess pressure, with the exclusion of light. The first half of the amount of chlorine calculated for dimethyltetrachlorobenzene was introduced into the gas chamber of the reaction vessel with the temperature of the liquid phase at 20°C, the remainder at 40°C. The reaction time was about 3 hours. Then, while irradiating the gas chamber in the reaction vessel with a 250-watt mercury vapor lamp at a temperature of 70°C in the liquid phase and 0.06 atmospheres excess pressure, the side chain chlorination was performed, which was completed within 4 hours 30 minutes. Total chlorine consumption: 110% of the calculated amount with respect to xylene. The reaction solution was stirred with 400 g of calcium hydroxide, rendering the solution neutral and iron-free. The calcium hydroxide containing iron and chloride was removed on a suction filter and the solution, after removal of the $CCl_4$ by distillation, was fractionated at 12 Torr in a packed column. The principal fraction distilled at 182°–187°C. 1125 g of 1-methyl-3-chloromethyl-2,4,5,6-tetrachlorobenzene was obtained in a purity of 95.3% (yield 77%).

After recrystallization from isopropanol + $CCl_4$ (1:1), the product had a purity of 98.4% and melted at 88°–89°C.

EXAMPLE 5

1-methyl-2-chloromethyl-3,4,5,6-tetrachlorobenzene 530 g of o-xylene in 5 liters of $CCl_4$ was chlorinated in the nucleus in the presence of 10 g of $FeCl_3$ by passing chlorine over the reaction solution while stirring the latter, at a pressure of 0.06 atmospheres excess pressure, with the exclusion of light. The first half of the amount of chlorine calculated for dimethyltetrachlorobenzene was introduced into the gas chamber of the reaction vessel at a liquid phase temperature of 20°C, and the remainder at 40°C. The reaction time was about 6 hours. Then, while irradiating the gas chamber in the reaction vessel with a 250-watt mercury vapor lamp at a liquid phase temperature of 70°C and 0.06 atmospheres excess pressure, the side-chain chlorination was performed, which required about 6 hours. Total chlorine consumption: 110% of the calculated amount, with respect to xylene. The reaction solution was stirred with 400 g of calcium hydroxide, which rendered the solution neutral and iron-free. The calcium hydroxide containing iron and chloride was removed on a suction filter and, after the $CCl_4$ had been removed by distillation, the solution was fractionated at 12 Torr in a packed column. The main fraction distilled at 179°–189°C. 1242 g of 1-methyl-2-chloromethyl-3,4,5,6-tetrachlorobenzene was obtained in a purity of 88.3% (yield 78.7%). After recrystallization from isopropanol + 1,2-dichloroethane (1:1), the product had a purity of 96.4% and melted at 102°–103°C.

EXAMPLE 6

1-methyl-4-chloromethyltetrachlorobenzene 530 g of p-xylene in 5 liters of $CCl_4$ were chlorinated in the nucleus in the presence of 10 g of $FeCl_3$ by passing chlorine over the reaction solution while stirring the latter, at a pressure of 0.06 atmospheres excess pressure, with the exclusion of light. The first half of the amount of chlorine calculated for dimethyltetrachlorobenzene was introduced into the gas chamber of the reaction vessel while the liquid phase was at a temperature of 20°C, the remainder at 40°C. The reaction time was 3 hours 30 minutes. Then, while the gas chamber in the reaction vessel was irradiated with a 250-watt mercury vapor lamp, the side-chain chlorination was performed at a liquid phase temperature of 70°C and at 0.06 atmospheres excess pressure; this required 6 hours. The total chlorine consumption was 110% of the calculated amount, with respect to xylene. After the solution cooled, 154 g of a substance crystallized, of which 75% consisted of 1,4-di-(chloromethyl)-2,3,5,6-tetrachlorobenzene. The crystallizate was suction filtered and the filtrate was stirred with 400 g of calcium hydroxide, thereby rendering the solution neutral and free of iron. The calcium hydroxide containing iron and chloride was removed on a suction filter and, after removing the $CCl_4$ by distillation, the solution was fractionated in a packed column at 12 Torr. The main fraction distilled at 179°–193°C. 1055 g of 1-methyl-4-chloromethyl-2,3,5,6-tetrachlorobenzene was obtained in a purity of 87.6% (yield 66.7%). After recrystallization from 1,2-dichloroethane, the product had a purity of 98.9% and melted at 111°–113°C.

EXAMPLE 7 (Comparative Example)

For the sake of comparison with the invention, Example 2 of German Pat. No. 1,568,607 is as follows: 1000 g of p-xylene + 3 g of $FeCl_3$ in 7000 ml of $CCl_4$ were chlorinated with stirring, at 40°–50°C. 3745 g of chlorine were introduced at a rate of 1070 g per hour. Then the mixture was heated on a water bath at 63° to 66°C, again with stirring, while being irradiated in the liquid phase with an 80-watt ultraviolet immersion lamp, and while another 2675 g of chlorine was passed through it over a period of 5 hours 15 minutes. The total reaction time amounted to 8 hours 45 minutes. The product was 1407 g of crystallizate, composition (by gas chromatography): 6.27% 1,4-dimethyltetrachlorobenzene; 74.5% 1-methyl-4-chloromethyltetrachlorobenzene; 18.9% 1,4-di-(chloromethyl)-tetrachlorobenzene. The filtrate obtained by suction filtering the crystallizate was washed free of FeCl$_3$ and, after removal of the CCl$_4$ by distillation, was vacuum-distilled. BP$_{12}$: 184°–216°C. 1196 g. Composition: 12.7% 1,4-dimethyltetrachlorobenzene; 73.4% 1-methyl-4-chloromethyltetrachlorobenzene; 11.4% 1,4-di-(chloromethyl)-tetrachlorobenzene. Total yield: 10.6% 1,4-dimethyltetrachlorobenzene; 74.4% 1-methyl-4-chloromethyltetrachlorobenzene and 13.7% 1,4-di-(chloromethyl)-tetrachlorobenzene.

What is claimed is:

1. A process for preparing a chloromethyltetrachlorobenzene which comprises the steps of:
    A. Contacting a xylene in a chlorine resistant solvent with greater than 1 and up to 2 weight percent of ferric chloride, based on the weight of said xylene, at a temperature of 20° to 70°C in the the absence of light in a vessel having a vapor space over the level of the xylene solution;
    B. Introducing into said vapor space gaseous chlorine and passing the same over said solution while strongly agitating the solution, said chlorine being introduced such that an excess pressure of 0.01 to 1 atmospheres exist over said solution;
    C. Maintaining said solution at said temperature of 20° to 70°C for a period of time of at least 0.5 hours.
    D. Thereafter directing energy-rich light at the vapor space over said solution while adding chlorine to said vapor space and maintaining the excess pressure over said solution at 0.01 to 1 atmospheres while maintaining the solution at a temperature of 50° to 80°C for a period of time of at least 0.5 hours and while continuing said agitation; and
    E. Separating and recovering chloromethyltetrachlorobenzene.

2. A process according to claim 1 wherein steps A-C are carried out with the exclusion of light admitted against the vapor space or the liquid phase while the liquid phase is maintained at a temperature of 20° to 40°C and step D is carried out at a temperature of 50° to 70°C.

3. A process according to claim 1 wherein the excess pressure in steps B and D is between 0.01 and 0.1 atmosphere.

4. A process according to claim 1 wherein the xylene is p-xylene.

5. A process according to claim 1 wherein the xylene is m-xylene.

6. A process according to claim 1 wherein the xylene is o-xylene.

7. A process according to claim 1 wherein the chlorine resistant solvent is carbon tetrachloride.

8. A process according to claim 1 wherein step C is carried out for between 3 and 6 hours.

9. A process according to claim 1 wherein step D is carried out for between 4 and 7 hours.

10. A process according to claim 1 wherein the amount of gaseous chlorine added is not more than 130% of the stoichiometric amount of chlorine for the desired chloromethyl tetrachlorobenzene.

* * * * *